(12) United States Patent
Das et al.

(10) Patent No.: US 10,212,299 B2
(45) Date of Patent: Feb. 19, 2019

(54) DETECTING A FOLDED PAGE IN A DIGITAL IMAGE OF A SCANNED DOCUMENT

(71) Applicant: Xerox Corporation, Norwalk, CT (US)

(72) Inventors: Arindam Das, West Bengal (IN); Ravindranath Mannuru, Andhra Pradesh (IN)

(73) Assignee: Xerox Corporation, Norwalk, CT (US)

( * ) Notice: Subject to any disclaimer, the term of this patent is extended or adjusted under 35 U.S.C. 154(b) by 9 days.

(21) Appl. No.: 15/433,736

(22) Filed: Feb. 15, 2017

(65) Prior Publication Data
US 2018/0234568 A1   Aug. 16, 2018

(51) Int. Cl.
*G01N 33/34*  (2006.01)
*G03G 15/00*  (2006.01)
*H04N 1/00*  (2006.01)
*G06T 7/13*  (2017.01)
*G01N 21/89*  (2006.01)

(52) U.S. Cl.
CPC ......... *H04N 1/00771* (2013.01); *G01N 21/89* (2013.01); *G01N 33/346* (2013.01); *G03G 15/706* (2013.01); *G06T 7/13* (2017.01); *H04N 1/00689* (2013.01); *H04N 1/00737* (2013.01); *H04N 1/00777* (2013.01); *H04N 1/00827* (2013.01); *G06T 2207/30176* (2013.01); *H04N 2201/0081* (2013.01); *H04N 2201/0082* (2013.01)

(58) Field of Classification Search
None
See application file for complete search history.

(56) References Cited

U.S. PATENT DOCUMENTS

| 2002/0150279 | A1* | 10/2002 | Scott | B65H 43/00 382/112 |
| 2008/0063240 | A1* | 3/2008 | Keng | G06K 9/036 382/112 |
| 2012/0194880 | A1* | 8/2012 | Muroi | H04N 1/00795 358/474 |

* cited by examiner

Primary Examiner — Benny Q Tieu
Assistant Examiner — Haris Sabah
(74) Attorney, Agent, or Firm — Philip E. Blair; Fleit Gibbons Gutman Bongini & Bianco P.L.

(57) ABSTRACT

What is disclosed is a system and method for detecting a folded page in a digital image of a scanned document. In one embodiment, the present method involves receiving a digital image of a document which has been converted to a digitized form using a document scanning device. The digital image is segmented horizontally and vertically to obtain a plurality of image segments. An edge profile is generated for the horizontal and vertical segments. A determination is then made, based on a comparison of the profiles, whether a page fold exists in the digital image. If a page fold is determined to exist in the digital image, the user is notified and the digital image is not sent to a print engine. Otherwise, the digital image is printed.

16 Claims, 11 Drawing Sheets

(19) United States
US 10,212,299 B2

DETECTING A FOLDED PAGE IN A DIGITAL IMAGE OF A SCANNED DOCUMENT

TECHNICAL FIELD

The present invention is directed to systems and methods for automatically detecting a folded page of a book placed on a platen of a document scanning device such that the user can be notified that a page fold has been detected and the folded page corrected before a digital image thereof is sent to the printer.

BACKGROUND

Obtaining a copy of a page of an open book requires that the book be opened and then placed face down on a platen of a document scanning device such as a flatbed scanner, and a copy operation initiated to reproduce the page by typically hitting a button labeled "COPY". The twin pages (left and right) of the open book are then scanned to obtain a digital image thereof. The digital image is sent to a print engine of the document scanner which proceeds to produce a copy/print and the user retrieves the printed copy from an output tray. When the user has many pages of a book to copy, the user flips to the desired pages, places the book face down on the platen, closes the lid, hits the COPY button, lifts the lid, flips to the next page in the book, and repeats the process until all the desired pages in the book have been reproduced. The user often doesn't know if a page fold has occurred until they've retrieved their printed copies from the device's output tray. When the user reviews their copies, they may notice that an inadvertent page fold exists in one of their copies. This requires that the user re-open the book to that particular page and repeat the process to obtain a corrected copy. This wastes time, paper, and toner and can lead to frustration. The teachings hereof are directed to automatically detecting a folded page in an image of a page or pages of a book that is placed face down on a platen of a document scanning device and then notifying the user that a page fold has been detected prior to the digital image of that page being sent to the print engine.

BRIEF SUMMARY

What is disclosed is a system and method for detecting a folded page in a digital image of a scanned document. In one embodiment, the present method involves receiving a digital image of a document which has been converted to a digitized form using a document scanning device. The digital image is segmented horizontally and vertically to obtain a plurality of image segments. In a manner more fully disclosed herein, an edge profile is generated for the horizontal and vertical segments. A determination is then made, based on a comparison of the profiles, whether a page fold exists in the digital image. If a page fold is determined to exist in the digital image, the user is notified and the digital image is not sent to a print engine. Otherwise, the digital image is printed.

Features and advantages of the above-described system and method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for automatically detecting a folded page in an image of a page of a book that is placed on a platen of a document scanning device and notifying the user that a page fold has been detected prior to the digital image of that page being sent to a print device.

Non-Limiting Definitions

A "digital image of a document", also referred to as a "digital document", refers to a digitized representation of a document. A digital image can be obtained using a document scanning device.

A "document scanning device", as are generally known, is a device which is used to obtain a digital image of a document such as a page of a book. Common document scanning devices include variations of the flatbed scanner which is widely used in various streams of commerce. Such devices consist of an image scanner to optically scan the face of a document, a display, and a user interface such as a touchscreen or a keypad for effectuating a user interaction through selectable buttons and menu options. Some image scanners use a charge-coupled device (CCD) which contains rows of sensors with filters such as (red, green, blue). Other image scanners use a contact image sensor (CIS) which consists of a moving set of strobed red, green, and blue LEDs and a monochromatic photodiode array for light collection. In operation, a user places a document to be scanned onto a glass pane (platen), closes the lid, and then presses, for instance, a "SCAN" button or selects a menu option from the device's LCD display. The optical scanner then moves across the document beneath the pane. Light reflected off the face of the document is detected by the sensor array. Specialized hardware and software receive data from the sensor array and form a digital image of the document. The digital image is typically then sent to a print engine that is internal to the document scanning device. The print engine applies ink or toner to a surface of a media such as xerographic paper to produce a hardcopy of print. One or more aspects of the present method may be performed by a processor or a special purpose ASIC integrated, in whole or in part, with a system or sub-system of a document scanning device which receives a digital image of the document for processing.

"Receiving a digital image" of a document is intended to be widely construed and includes: retrieving, acquiring, or otherwise obtaining a digital image for processing in accordance with the methods disclosed herein. The teachings hereof are directed to detecting a page fold in one or more pages of a received digital image.

Figure 1:
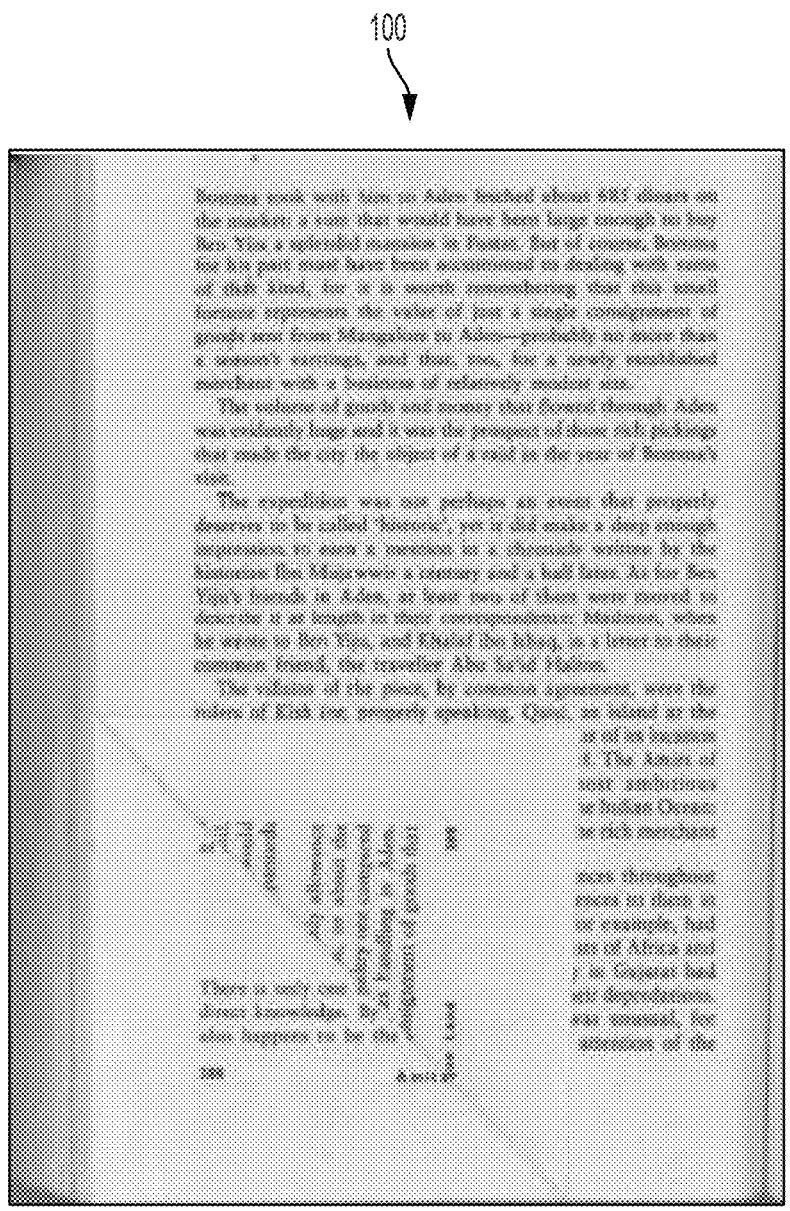
FIG. 1 shows a first digital image of a scanned page of a book which contains an inadvertent page fold.
Figure 2:
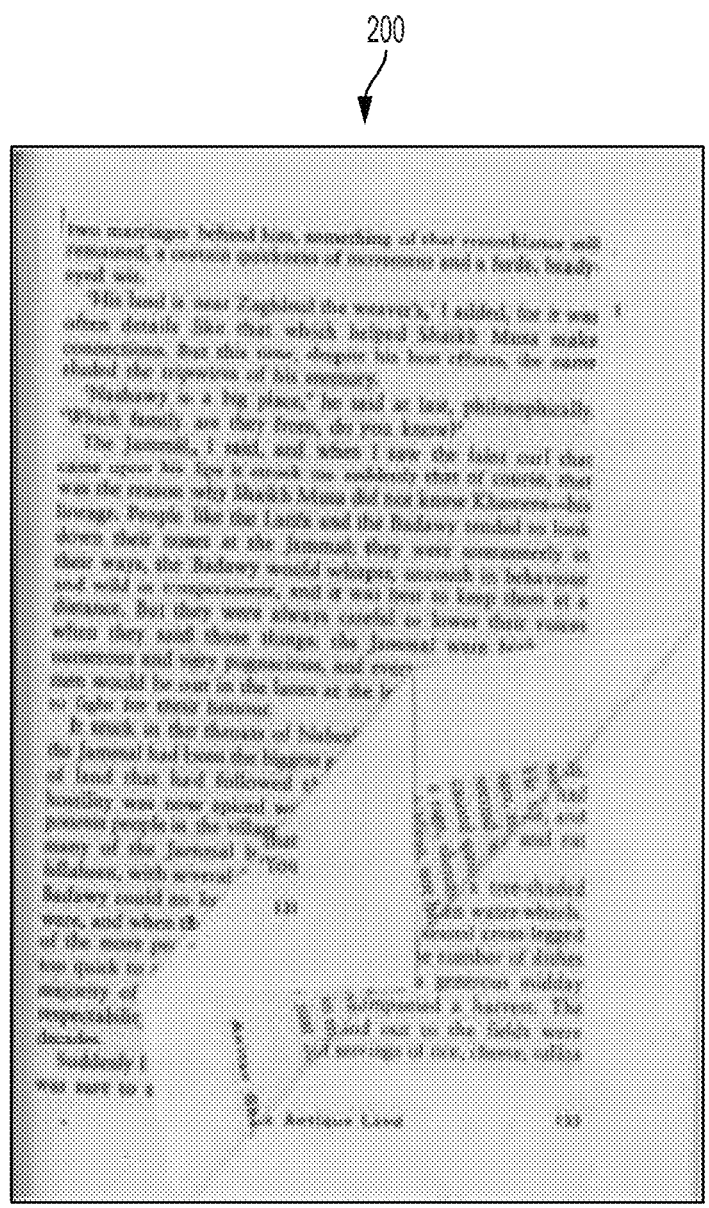
FIG. 2 shows a second digital image of a scanned page of a book which contains an inadvertent page fold.

A "page fold" or "folded page" is shown by way of example in FIGS. 1 and 2. FIG. 1 shows a digital image of a left page 100 of a book. FIG. 2 shows a digital image of a right page 200 of a book. As discussed in the background hereof, the page fold occurred when a user incorrectly placed the pages of an open book on the platen of the document scanning device. The received digital image is segmented into a plurality of horizontal and vertical image segments. In various embodiments hereof, the digital image is first pre-processed prior to image segmentation.

Figure 3:
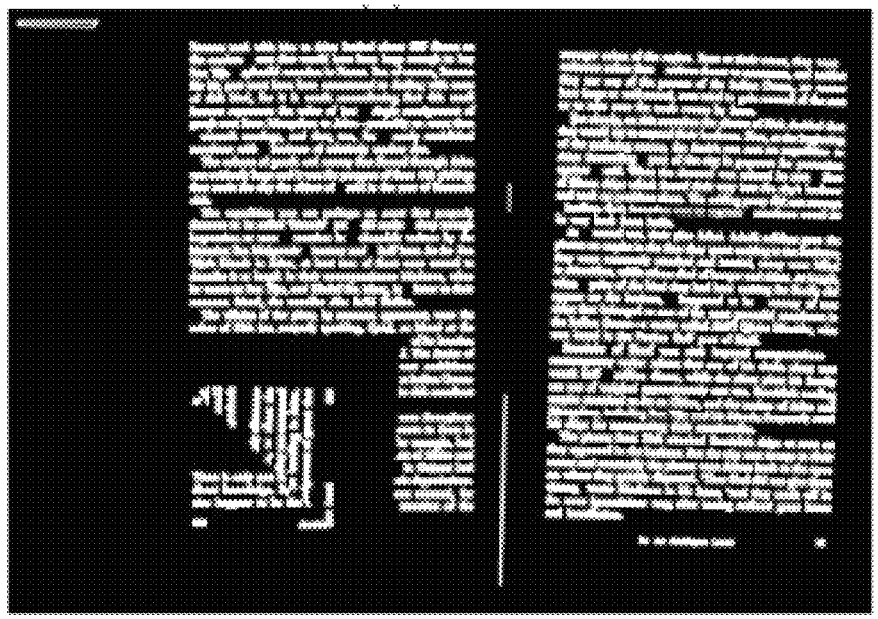
FIG. 3 shows the left and right pages of FIGS. 1 and 2 having been pre-processed according to various embodiments hereof.

"Processing the digital image" means manipulating the pixels in the digital image to obtain a pre-processed image. FIG. 3 shows a digital image containing the left and right pages of FIGS. 1 and 2 having been pre-processed. In one embodiment, processing involves converting the digital image to an equivalent greyscale by transforming each input pixel to a modified output pixel in a manner that is grey level dependent. A complement operation may be performed on the obtained greyscale image to reverse brightness levels. This produces the equivalent of a negative of the image. Some complement algorithms utilize a simple relationship to compute values of target pixels. One such relationship takes the form:

Input_Pixel($x,y$)=255−Output_Pixel($x,y$).

Processing the digital image may also involve converting the received digital image or converting the complementary image to a binary image. A flood-fill operation and/or dilating the image can also be performed. Methods for processing a digital image to obtain a pre-processed image are well known in the image processing arts. Noise can be removed by, for example, locating spurious pixels in the image and deleting them by changing their values to match the value of pixels in a background of the image. The received digital image is segmented to obtain a plurality of horizontal and vertical segment.

Figure 4:
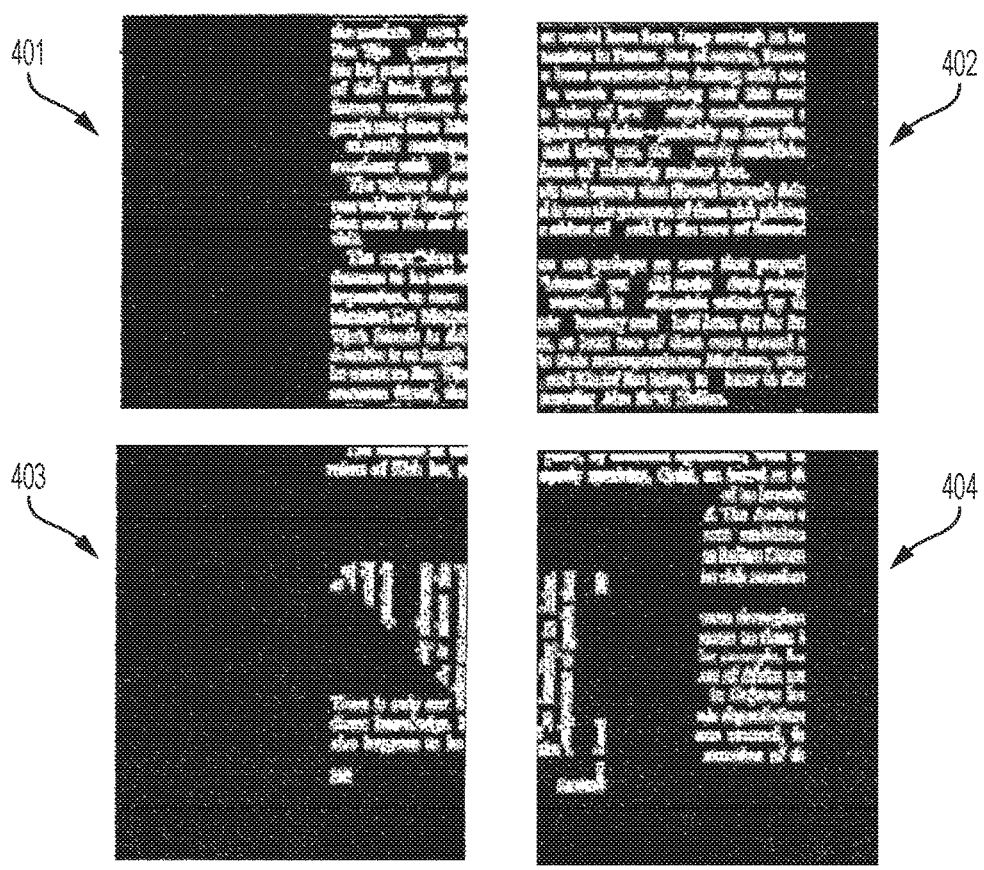
FIG. 4 shows the left page of the pre-processed digital image of FIG. 3 having been segmented vertically and horizontally into a plurality of image segments.

"Segmenting an image" means to divide the digital image horizontally and vertically into a plurality of image segments. FIG. 4 shows the left page of the pre-processed image of FIG. 3 having been divided horizontally and vertically into a plurality of image segments. The segments are processed to obtain edge profiles.

Figure 5A:
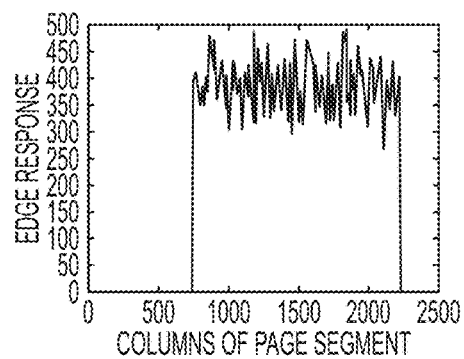
FIGS. 5A-B are graphical representations of the horizontal edge profiles generated for the image segments 401 and 402, respectively.
Figure 5B:
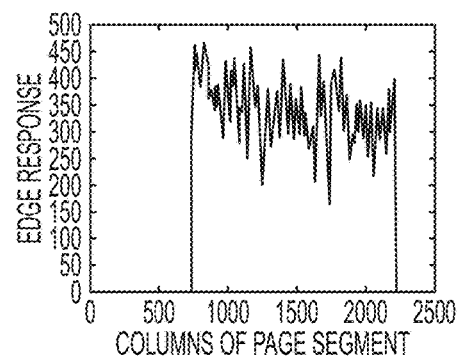
Figure 5C:
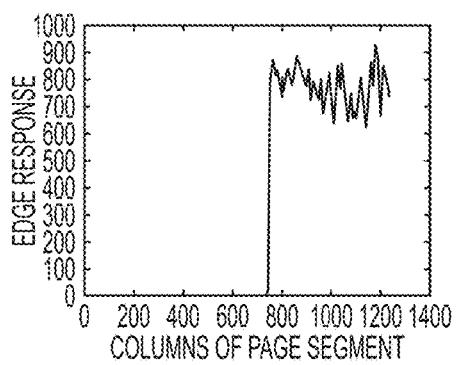
FIGS. 5C-D are graphical representations of the vertical edge profiles generated for the image segments 401 and 402, respectively.
Figure 5D:
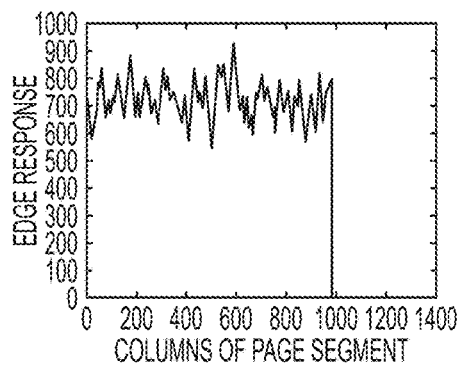
Figure 5E:
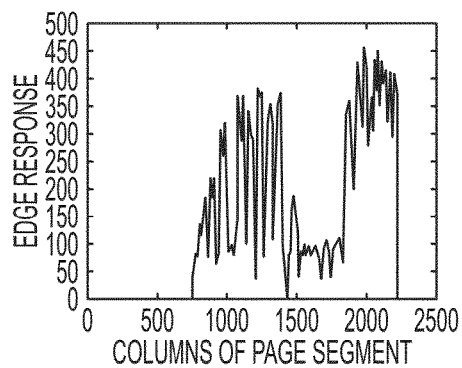
FIGS. 5E-F are graphical representations of the horizontal edge profiles generated for the image segments 403 and 404, respectively.
Figure 5F:
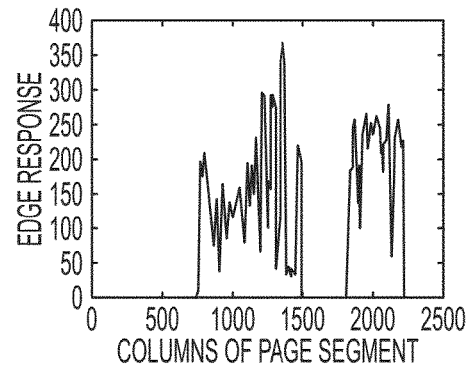

An "edge profile for a horizontal segment", also referred to as a "horizontal edge profile", is generated by summing up values of pixels in each column of that segment to obtain a single row matrix. FIGS. 5A-B are graphical representations of the horizontal edge profiles generated for the image segments 401 and 402, respectively. FIGS. 5E-F are graphical representations of the horizontal edge profiles generated for the image segments 403 and 404, respectively.

Figure 5G:
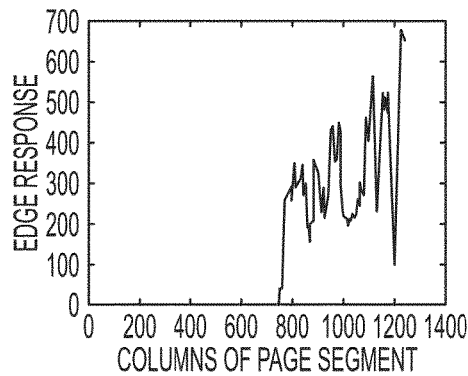
FIGS. 5G-H are graphical representations of the vertical edge profiles generated for the image segments 403 and 404.
Figure 5H:
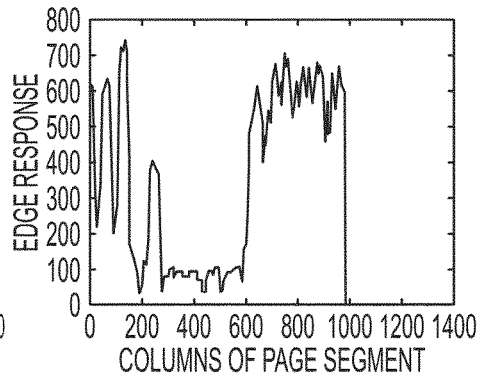

An "edge profile for a vertical segment", also referred to as a "vertical edge profile", is generated by summing up values of pixels in each row of that segment to obtain a single column matrix. FIGS. 5C-D are graphical representations of the vertical edge profiles generated for the image segments 401 and 402, respectively. FIGS. 5G-H are graphical representations of the vertical edge profiles generated for the image segments 403 and 404.

Figure 6A:
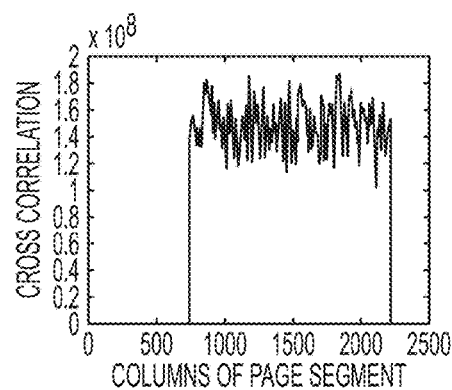
FIG. 6A shows a graphical representation of the cross correlation determined between the edge profiles of FIGS. 5A and 5C.
Figure 6B:
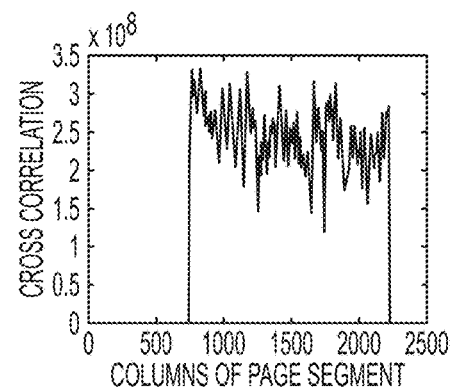
FIG. 6B shows a graphical representation of the cross correlation determined between the edge profiles of FIGS. 5B and 5D.
Figure 6C:
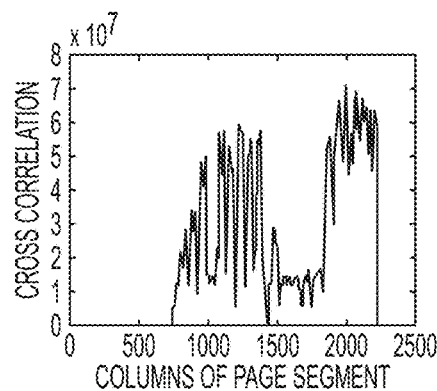
FIG. 6C shows a graphical representation of the cross correlation determined between the edge profiles of FIGS. 5E and 5G.
Figure 6D:
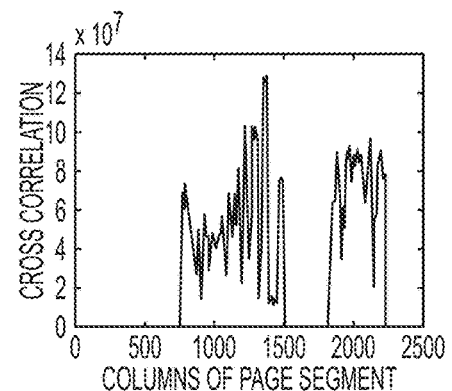
FIG. 6D shows a graphical representation of the cross correlation determined between the edge profiles of FIGS. 5F and 5H.
Figure 7:
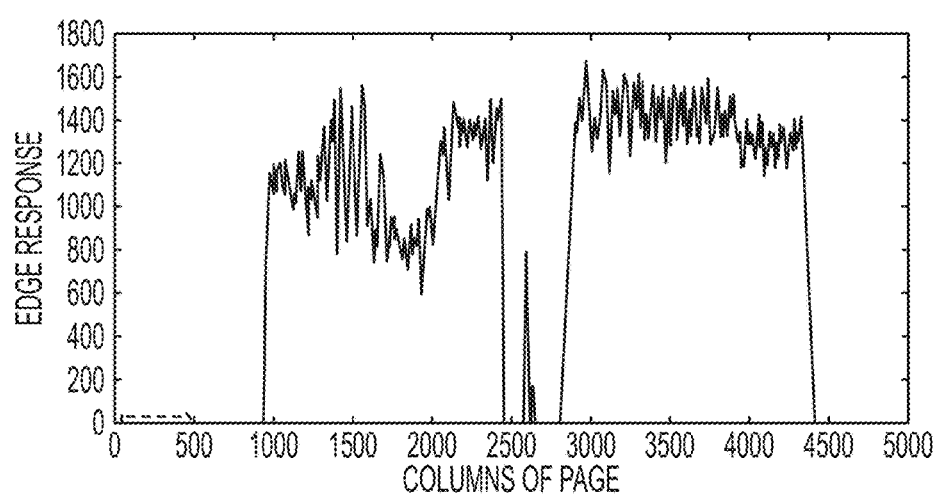
FIG. 7 is a graphical representation which shows a discontinuity in the horizontal edge profile of the digital image.

"Determining based on the profiles" whether a page fold exists means to analyze the edge profiles to determine an amount of cross correlation between the edge profiles generated for each horizontal and vertical segment. This can be effectuated using, for instance, a 2-D cross correlation technique. Here we find the similarity between one horizontal and one vertical profile on a per-segment basis. Correlation will be checked between the horizontal edge profile of FIG. 5A and the vertical edge profile of FIG. 5C. The correlation will be checked between the horizontal edge profile of FIG. 5B and the vertical edge profile of FIG. 5D. Likewise, the correlation will also be checked for FIG. 5E vs FIG. 5G, and FIG. 5F vs FIG. 5H. The resultant realizations are column-wise summed up. The results after performing this correlation check are shown in FIGS. 6A-D. FIG. 6A is a graphical representation of the correlation determined between the edge profiles of FIGS. 5A and 5C. FIG. 6B is a graphical representation of the correlation determined between the edge profiles of FIGS. 5B and 5D. FIG. 6C is a graphical representation of the correlation determined between the edge profiles of FIGS. 5E and 5G, and FIG. 6D shows the correlation determined between the edge profiles of FIGS. 5F and 5H. As can be seen in FIGS. 6A and 6B, there is good cross correlation between the horizontal and vertical edge profiles of the image segments 401 and 402. But FIGS. 6C and 6B show that there are discontinuities between the horizontal and vertical edge profiles of the image segments 402 and 403, thereby indicating that a page fold has been detected in the bottom portion of the page. FIG. 7

Figure 8:
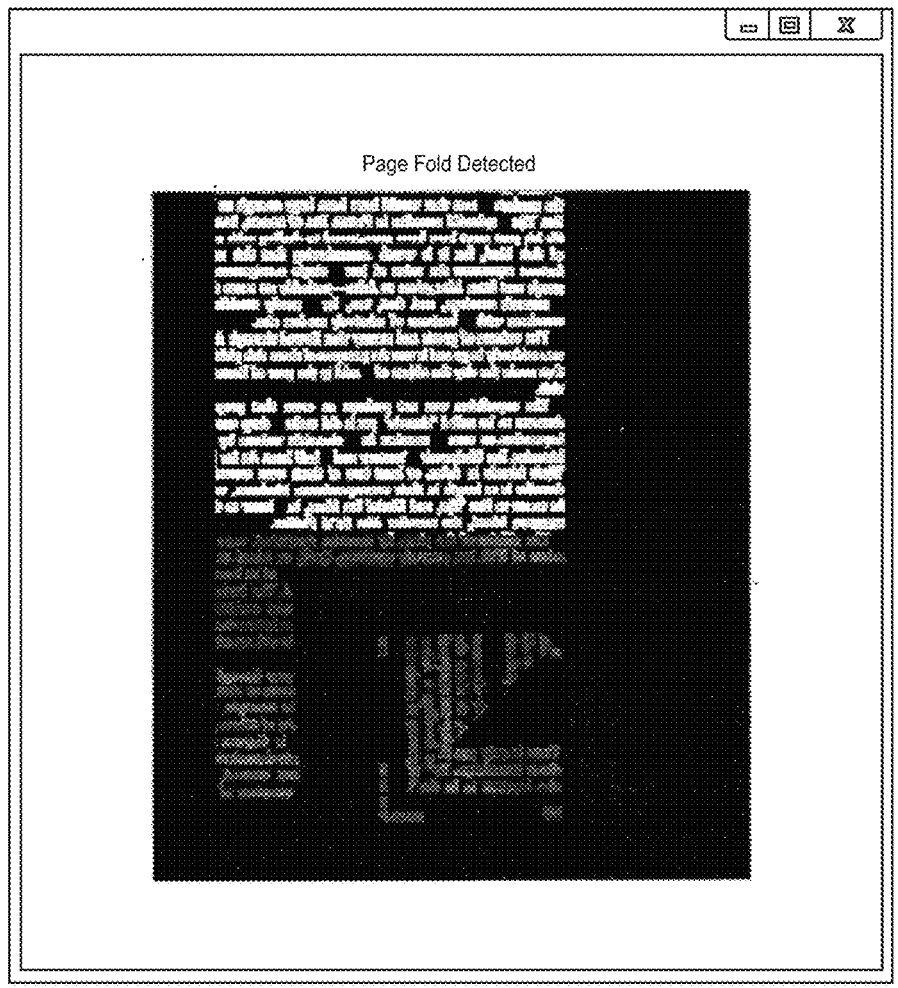
FIG. 8 shows an example message which takes the form of a page containing the detected page fold.

"Communicating a message" to a user that a page fold has been detected includes displaying text on the user interface of the document scanning device, sending them a text message to their smartphone, blinking a visually perceptible light, or making an audible noise. Such a message may further take the form of the detected page fold, as shown in FIG. 8, with the portion of the digital image containing the detected page fold being highlighted or colored for the user's convenience.

A "storage device" refers to a drive, device, or system which electronically stores digital documents. Storage devices include memory such as ROM, RAM, FLASH, to name a few, and devices such a floppy disk, hard drive, and other removable storage media useful for transporting data and for retrieving machine readable program instructions.

A "processor" is a device capable of retrieving machine readable program instructions from a storage device which, when executed by the processor, configure the processor to perform various aspects of the teachings disclosed herein. A processor is intended to encompass multi-core, multi-threaded, and multi-processor systems and devices It should be appreciated that the steps of "receiving", "segmenting", "generating", "dividing", "performing", "preventing", "determining", "communicating", and the like, as used herein, include the application of any of a variety of techniques as well as mathematical operations according to any specific context or for any specific purpose. It should be appreciated that such steps may be facilitated or otherwise effectuated by a microprocessor executing machine readable program instructions such that the intended functionality is effectively performed.

Flow Diagram of One Embodiment

Figure 9:
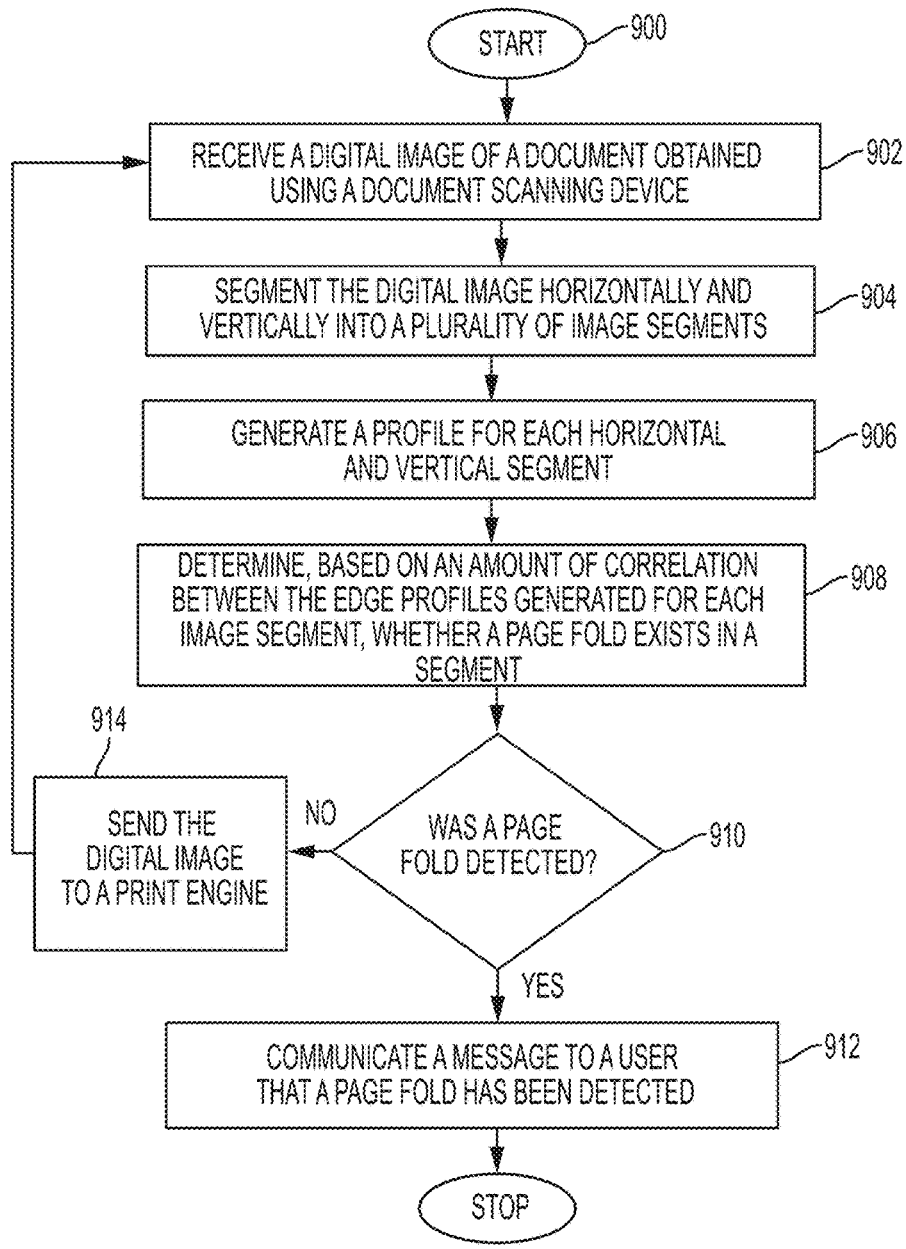
FIG. 9 is a flow diagram which illustrates one embodiment of the present method for detecting a folded page of a book placed on a platen of a document scanning device.

Reference is now being made to the flow diagram of FIG. 9 which illustrates one embodiment of the present method for automatically detecting a folded page of a book placed on a platen of a document scanning device. Flow processing begins at step 1400 and immediately proceeds to step 902.

At step 902, receive a digital image of a document obtained using a document scanning device. Example received digital images are shown in FIGS. 1 and 2. The digital image may be retrieved from a memory or storage device, from a media such as a CDROM or DVD, or from a remote device such as a handheld computing device or smartphone over a wired or wireless network.

At step 904, segment the digital image into a plurality of image segments. An example digital image that has been divided into a plurality of image segments is shown in FIG. 4.

At step 906, generate an edge profile for each horizontal and vertical segment. Various graphical representations of edge profiles generated for horizontal and vertical segments are shown in FIGS. 5A-H.

At step 908, determine, based on an amount of correlation between the edge profiles generated for each image segment, whether a page fold exists in a segment. Graphical representations of the correlations determined as a result of the comparisons of various horizontal and vertical edge profiles are shown in FIGS. 6A-D.

At step 910, a determination is made whether a page fold was detected. If a page fold exists in the digital image then, at step 912, communicate a message to a user that a page fold has been detected. One example message that is communicated to the user upon a page fold being detected is shown in FIG. 8. In this embodiment, further processing stops. Otherwise, if a page fold is not detected then processing continues with respect to step 914.

At step 914, send the digital image to a print engine. Processing continues thereafter with respect to step 902 wherein a next digital image is received for processing. Processing repeats in a similar manner until the user has no more pages to copy. Thereafter, further processing stops.

It should be appreciated that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Example Networked System

Figure 10:
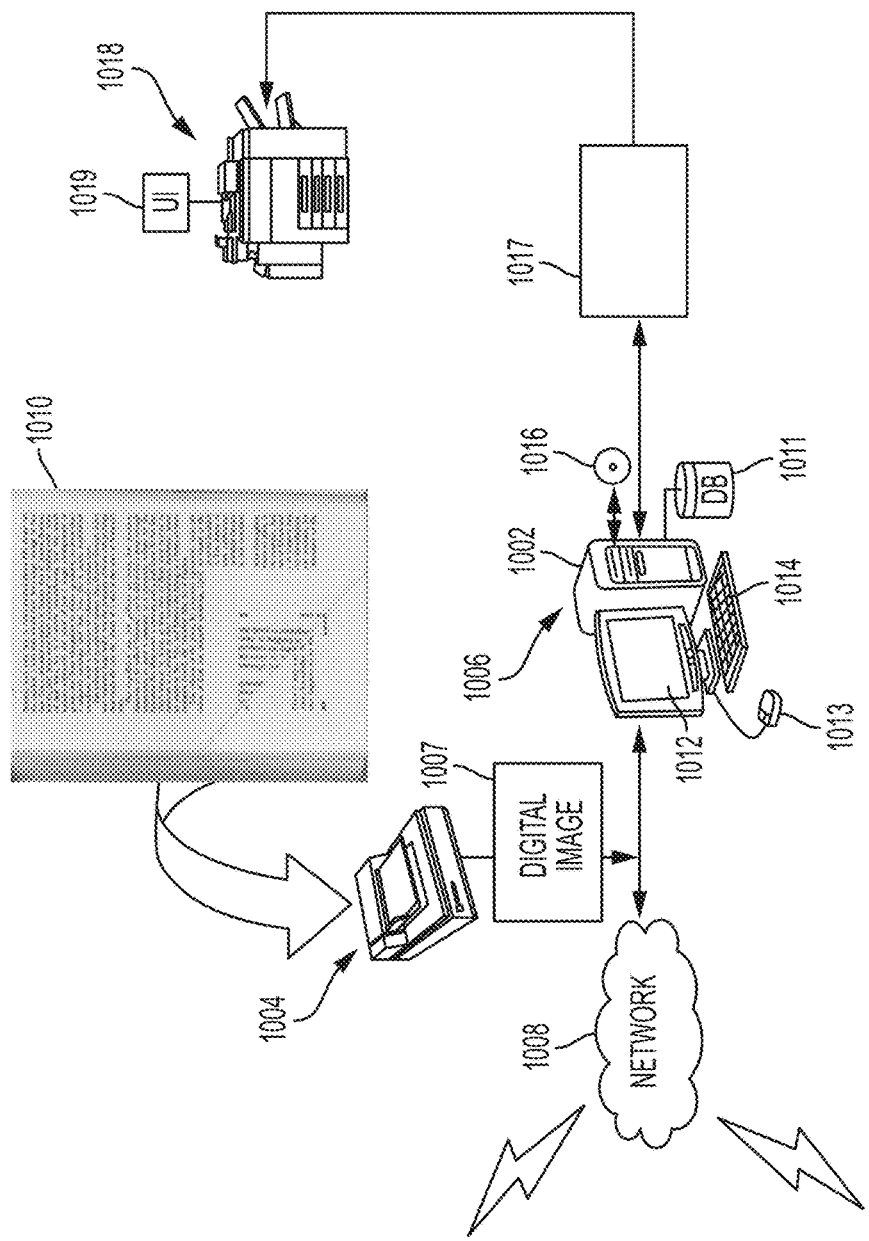
FIG. 10 is a functional block diagram of an example networked system configured to perform various aspects of the present method as shown and described with respect to the flow diagram of FIG. 9.

Reference is now being made to FIG. 10 which shows a functional block diagram of an example networked system configured to perform various aspects of the present method as shown and described with respect to the flow diagram of FIG. 9.

Hardcopy document 1010 is placed on the platen of document scanning device 1004 which is an embodiment of a flatbed scanner known in the arts. Specialized sensors move beneath the platen to scan the document placed thereon in order to generate a digital image 1007 of the document. In this embodiment, digital image 1007 is communicated to computer workstation 1006 for processing. The digital image may also be provided to one or more remote devices (not shown) which have been placed in communication with the document scanning device 1006 over network 1008. Workstation 1006 may alternatively retrieve the digital image from storage devices 1011 or 1016.

The computer workstation includes a hard drive (internal to computer housing 1002) which reads/writes to a computer readable media 1016 such as a floppy disk, optical disk, CD-ROM, DVD, etc. Case 1002 houses a motherboard with a processor and memory, a communications link such as a network card, graphics card, and the like, and other software and hardware to perform the functionality of a computing device as is generally known in the arts. The workstation includes a graphical user interface which, in various embodiments, comprises display 1012 such as a CRT, LCD, touch screen, etc., mouse 1013, and keyboard 1014. It should be appreciated that the workstation has an operating system and other specialized software configured to display a wide variety of numeric values, text, pull-down menus, and the like, with selectable options for entering, selecting, or modifying information on the display. The embodiment shown is only illustrative. Although shown as a desktop computer, it should be appreciated that the computer workstation can be any of a laptop, mainframe, client/server, or a special purpose computer such as an ASIC, circuit board, dedicated processor, or the like. The digital image, including various characteristics thereof, can be displayed to the user. Any information about the document image may be communicated to a remote device over network 1008 for storage or processing. It should be appreciated that some or all of the functionality performed by the workstation to process a digital image in accordance with the methods disclosed herein can be performed, in whole or in part, by a processor internal to the document scanning device may reside on hardware designed to perform the intended functionality hereof, in conjunction with machine readable program instructions. The embodiment shown is illustrative and should not be viewed as limiting the scope of the appended claims strictly to that configuration.

Network 1008 is shown as an amorphous cloud. A detailed discussion as to the operation of any specific network or a network configuration has been omitted. Suffice it to say, packets of data are transmitted over the network via special purpose devices in communication with each other via a plurality of communication links. Data is transferred between devices in the network in the form of signals. Such signals may be in any combination of electrical, electro-magnetic, optical, or other forms, and are transmitted by wire, cable, fiber optic, phone line, cellular link, RF, satellite, or any other medium or communications link known in the arts.

In the embodiment of FIG. 10, the workstation communicates the digital image 1017 to a printer 1018 which proceeds to render a hardcopy print of the scanned digital document. Alternatively, in response to a page fold existing, the image 1017 takes the form of a message containing an image of the detected page fold (as shown in FIG. 8) which is communicated to the display (UI) 1019. Such a notification message may be communicated to the display device 1012 of the workstation or sent to the user's smartphone in the form of an email, text, or audio message via communication pathways of the network 1008.

The teachings hereof can be implemented in hardware or software using any known or later developed systems, processors, devices, and/or software by those skilled in the applicable arts without undue experimentation from the functional description provided herein with a general knowledge of the relevant arts. It will be appreciated that the above-disclosed and other features and functions, or alternatives thereof, may be desirably combined into other different systems or applications.

One or more aspects of the system and methods described herein are intended to be incorporated in an article of manufacture which may be shipped, sold, leased, or otherwise provided separately either alone or as part of a product suite or a service by the assignee or a licensee hereof.

Presently unforeseen or unanticipated alternatives, modifications, variations, or improvements may become apparent and/or subsequently made by those skilled in this art which are intended to be encompassed by the following claims. The teachings of any publications referenced herein are hereby incorporated by reference in their entirety.

What is claimed is:

1. A computer implemented method for detecting a folded page in a digital image, the method comprising:
    scanning, by a document scanning device, a document to generate the digital image of that document; and
    a processor executing machine readable program instructions stored in a storage device which, when executed, configure the processor to: receive the digital image from the document scanning device;
    segment the digital image into four image sections consisting of an upper left portion, an upper right portion, a lower left portion and a lower right portion;
    divide each of the four image sections horizontally into a plurality of horizontal segments and then dividing the horizontal segments into a plurality of vertical segments;
    generate, for each horizontal segment, a horizontal edge profile by summing values of pixels in each column of a horizontal edge for each of the horizontal segment to obtain a single row matrix;
    generate, for each vertical segment, a vertical edge profile by summing the values of the pixels in each row of a vertical edge for each of the vertical segment to obtain a single column matrix;
    determine, based on an amount of 2-D cross correlation between the horizontal edge profile and the vertical edge profile generated for each horizontal and vertical segment, whether a page fold exists in the digital image; and
    in response to the page fold existing in the digital image, communicate a message to a display device that the page fold has been detected.

2. The computer implemented method of claim 1, wherein, in advance of segmenting the digital image, the processor being further configured to:
    convert the digital image to an equivalent greyscale image and then complementing the greyscale image to obtain a complemented digital image; and
    generate a binary image from the complemented digital image and then performing a flood-fill operation on the binary image.

3. The computer implemented method of claim 1, wherein, in response to the page fold existing in the digital image, the processor being further configured to prevent the digital image from being printed, otherwise the processor being further configured to communicate the digital image to any of: a print engine and the storage device.

4. The computer implemented method of claim 1, wherein the message takes a form of an image containing the detected page fold.

5. A system for detecting a folded page in a digital image, the system comprising:
    a document scanner to generate the digital image of a document; and
    a processor executing machine readable program instructions stored in a storage device which, when executed, configure the processor to:
    receive the digital image from the document scanner;
    segment the digital image into four image sections consisting of an upper left portion, an upper right portion, a lower left portion and a lower right portion;
    divide each of the four image sections horizontally into a plurality of horizontal segments and then dividing the horizontal segments into a plurality of vertical segments;
    divide the digital image vertically into a plurality of vertical segments and then dividing the vertical segments into a plurality of horizontal segments;
    generate, for each horizontal segment, a horizontal edge profile by summing values of pixels in each column of a horizontal edge for each of the horizontal segment to obtain a single row matrix;
    generate, for each vertical segment, a vertical edge profile by summing the values of the pixels in each row of a vertical edge for each of the vertical segment to obtain a single column matrix;
    determine, based on an amount of 2-D cross correlation between the horizontal edge profile and the vertical edge profile generated for each horizontal and vertical segment, whether a page fold exists in the digital image; and
    in response to the page fold existing in the digital image, communicate a message to a display device that the page fold has been detected.

6. The system of claim 5, wherein, in advance of segmenting the digital image, the processor being further configure to:
    convert the digital image to an equivalent greyscale image and then complement the greyscale image to obtain a complemented digital image; and
    generate a binary image from the complemented digital image and then perform a flood-fill operation on the binary image.

7. The system of claim 5, wherein, in response to the page fold existing in the digital image, the processor being further configured to prevent the digital image from being printed, otherwise the processor being further configured to communicate the digital image to any of: a print engine and the storage device.

8. The system of claim 5, wherein the message takes a form of an image containing the detected page fold.

9. A computer implemented method for detecting a folded page in a digital image, the method comprising:
- scanning, by a document scanning device, a document to generate the digital image of that document; and
- a processor executing machine readable program instructions stored in a storage device which, when executed, configure the processor to:
- receive the digital image from the document scanning device;
- segmenting the digital image into four image sections consisting of an upper left portion, an upper right portion, a lower left portion and a lower right portion;
- divide each of the four image sections horizontally into a plurality of horizontal segments and then dividing the horizontal segments into a plurality of vertical segments;
- generate, for each horizontal segment, a horizontal edge profile by summing values of pixels in each column of a horizontal edge for each of the horizontal segment to obtain a single row matrix;
- generate, for each vertical segment, a vertical edge profile by summing the values of the pixels in each row of a vertical edge for each of the vertical segment to obtain a single column matrix;
- determine, based on an amount of 2-D cross correlation between the horizontal edge profile and the vertical edge profile generated for each horizontal and vertical segment, whether a page fold exists in the digital image; and
- in response to the page fold existing in the digital image, communicate a message to a display device that the page fold has been detected.

10. The computer implemented method of claim 9, wherein, in advance of segmenting the digital image, the processor being further configured to:
- convert the digital image to an equivalent greyscale image and then complementing the greyscale image to obtain a complemented digital image; and
- generate a binary image from the complemented digital image and then performing a flood-fill operation on the binary image.

11. The computer implemented method of claim 9, wherein, in response to the page fold existing in the digital image, the processor being further configured to prevent the digital image from being printed, otherwise the processor being further configured to communicate the digital image to any of: a print engine and the storage device.

12. The computer implemented method of claim 9, wherein the message takes a form of an image containing the detected page fold.

13. A system for detecting a folded page in a digital image, the system comprising:
- a document scanner to generate the digital image of a document; and
- a processor executing machine readable instructions stored in a storage device which, when executed, configure the processor to:
- receive the digital image from the document scanner;
- segment the digital image into four image sections consisting of an upper left portion, an upper right portion, a lower left portion and a lower right portion;
- divide each of the four image sections horizontally into a plurality of horizontal segments and then dividing the horizontal segments into a plurality of vertical segments;
- generate, for each horizontal segment, a horizontal edge profile by summing values of pixels in each column of a horizontal edge for each of the horizontal segment to obtain a single row matrix;
- generate, for each vertical segment, a vertical edge profile by summing the values of the pixels in each row of a vertical edge for each of the vertical segment to obtain a single column matrix;
- determine, based on an amount of 2-D cross correlation between the horizontal edge profile and the vertical edge profile generated for each horizontal and vertical segment, whether a page fold exists in the digital image; and
- in response to the page fold existing in the digital image, communicate a message to a display device that the page fold has been detected.

14. The system of claim 13, wherein, in advance of segmenting the digital image, the processor being further configure to:
- convert the digital image to an equivalent greyscale image and then complement the greyscale image to obtain a complemented digital image; and
- generate a binary image from the complemented digital image and then perform a flood-fill operation on the binary image.

15. The system of claim 13, wherein, in response to the page fold existing in the digital image, the processor being further configured to prevent the digital image from being printed, otherwise the processor being further configured to communicate the digital image to any of: a print engine and the storage device.

16. The system of claim 13, wherein the message takes a form of an image containing the detected page fold.

* * * * *